United States Patent [19]

Stauffer

[11] Patent Number: 5,854,168
[45] Date of Patent: Dec. 29, 1998

[54] CATALYST COMPOSITION FOR METHANOL SYNTHESIS

[76] Inventor: John E. Stauffer, 6 Pecksland Rd., Greenwich, Conn. 06831

[21] Appl. No.: 970,021

[22] Filed: Nov. 13, 1997

[51] Int. Cl.$^6$ .......................... B01J 27/122; B01J 23/70; C07C 27/00
[52] U.S. Cl. .......................... 502/225; 502/345; 568/893
[58] Field of Search .................................. 502/225, 345; 568/393

[56] References Cited

U.S. PATENT DOCUMENTS

| | | | |
|---|---|---|---|
| 4,172,838 | 10/1979 | Garnett et al. | 549/505 |
| 5,185,479 | 2/1993 | Stauffer . | |

FOREIGN PATENT DOCUMENTS 54024827  2/1979  Japan .

OTHER PUBLICATIONS

Linus Pauling, The Nature Of The Chemical Bond, Book, 1948, p. 53, Cornell University Press, Ithica, New York.

*Primary Examiner*—Gary Geist
*Assistant Examiner*—J. Parsa
*Attorney, Agent, or Firm*—Young & Basile, P.C.

[57] ABSTRACT

A new catalyst composition is provided for the synthesis of methyl alcohol by a catalytic reaction where methyl chloride, perchloroethylene, hydrogen chloride, and oxygen are converted to methyl alcohol and hexachloroethylene. The catalyst composition is an admixture of an iodine salt with copper chloride enhanced as needed by a chloride of iron, zinc, lead or bismuth or an admixture of an alkali metal bromine salt such as sodium bromide, potassium bromide and cesium bromide substituted for the iodine salt.

3 Claims, No Drawings

CATALYST COMPOSITION FOR METHANOL SYNTHESIS

FIELD OF THE INVENTION

A new and improved catalyst composition has been developed for the synthesis of methyl alcohol via a process comprising two steps: 1. the catalytic reaction whereby methyl chloride, perchloroethylene, hydrogen chloride, and oxygen are converted to methyl alcohol and hexachloroethane, and 2. the thermal chlorination of methane with hexachloroethane to give methyl chloride, hydrogen chloride and perchloroethylene. The new catalyst composition used in the first step comprises an admixture of an iodine salt with copper chloride enhanced, as needed, by other metal chlorides selected from the group, potassium chloride, iron chloride, zinc chloride, lead chloride and bismuth chloride. In another embodiment of this invention, a bromine salt is substituted for the iodine salt. The new catalyst composition has the advantage of substantially increasing the rate of the catalytic reaction, thereby improving the economics of the process.

BACKGROUND OF THE INVENTION

In U.S. Pat. No. 5,185,479, a process was disclosed for the synthesis of methyl alcohol from methane using two reaction steps operated in tandem. In the first reaction step, two chemical reactions occur simultaneously: a) perchloroethylene ($CCl_2=CCl_2$) is oxychlorinated with hydrogen chloride and oxygen to obtain hexachloroethane ($CCl_3CCl_3$) and water, and b) methyl chloride ($CH_3C$ 1) is hydrolyzed with water to give methyl alcohol ($CH_3OH$) and hydrogen chloride. In the second reaction step, methane is chlorinated with hexachloroethane to produce methyl chloride, hydrogen chloride, and perchloroethylene. By recycling the methyl chloride, hydrogen chloride and regenerated perchloroethylene produced in the second step to the first step, the process can be operated continuously in a balanced mode whereby there is no net consumption nor production of hydrogen chloride.

A critical factor in the process is the choice of catalyst used in the first reaction step. For some time, copper chloride has been known to be an effective catalyst for oxychlorination. This catalyst is generally enhanced by the addition of other metal chlorides including salts of iron, potassium, lead and rare earths. Copper chloride also is an effective catalyst for the hydrolysis of methyl chloride. Zinc chloride, however, is even more active. Another catalyst which may be used in the hydrolysis reaction is bismuth chloride. Thus, for the combined catalytic reaction comprising both oxychlorination and hydrolysis, the catalyst of choice was specified as copper chloride enhanced by other metal chlorides selected from the group, potassium chloride, iron chloride, zinc chloride, lead chloride, and bismuth chloride.

Notwithstanding the extensive literature on catalyst development, the results were seen to be less than satisfactory. The primary concern was the stability of methyl chloride. This compound, for example, is less reactive than either methylene chloride or ethyl chloride. Methyl chloride resists hydrolysis under the reaction conditions, namely, operating temperatures in the range of 200° to 375 ° C. Attempts to change these conditions are frustrated by thermodynamic restrictions. Thus, the relative inertness of methyl chloride leads to an excessively slow reaction rate in the first reaction step.

Therefore it is an object of the present invention to overcome the limitations of the prior art by providing an improved catalyst composition with high activity.

Furthermore, it is an object to provide a catalyst composition with favorable physical properties.

These and other objects, features and advantages of the invention will be apparent from the following description.

SUMMARY OF THE INVENTION

The invention in one preferred embodiment concerns a new catalyst composition for the conversion of methyl chloride, perchloroethylene, hydrogen chloride and oxygen to methyl alcohol and hexachloroethane. The new catalyst composition comprises copper chloride enhanced by an iodine salt as the co-catalyst. The iodine salt may be an alkali metal iodide, for example, sodium iodide, potassium iodide, or cesium iodide. The preferred level of addition of iodine salt to the catalyst composition is in the range of 0 to 25 weight percent, the effect of such iodide being pronounced in low concentrations.

The new catalyst composition may contain one metal chloride or more in conjunction with the copper chloride. Such additional metal chlorides include potassium chloride, iron chloride, zinc chloride, lead chloride, and bismuth chloride. In place of an iodine salt, the new catalyst composition may contain a bromine salt. Such bromine salt may be an alkali metal bromide, including sodium bromide, potassium bromide, and cesium bromide.

When the catalyst composition is subjected to the oxidizing conditions of the first reaction step, cupric oxyhalide is formed. In the case of an iodine salt being used as a cocatalyst, the cupric oxyhalide has the formula CuICl·CuO. If a bromine salt is substituted for the iodine salt, the cupric oxyhalide will be CuBr Cl·CuO. By undergoing reactions with the process intermediates, the oxyhalide determines the reaction kinetics.

DETAILED DESCRIPTION OF THE INVENTION

The advantages of using the new catalyst composition for methanol synthesis can be understood from the mechanism of the reaction of methyl chloride, perchloroethylene, hydrogen chloride, and oxygen to produce methyl alcohol and hexachloroethane. This reaction mechanism is illustrated by the following equations:

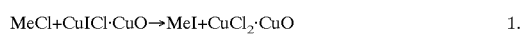
MeCl+CuICl·CuO→MeI+CuCl₂·CuO                              1.

MeI+H₂O→MeOH+HI                                            2.

HI+HCl+CuCl₂·CuO→CuCl₂·CuICl+H₂O                           3.

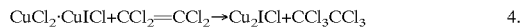
CuCl₂·CuICl+CCl₂=CCl₂→Cu₂ICl+CCl₃CCl₃                      4.

Cu₂ICl+½O₂→CuICl·CuO                                       5.

The net reaction of the above equations is represented by the following expression:

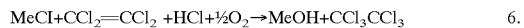
MeCl+CCl₂=CCl₂ +HCl+½O₂→MeOH+CCl₃CCl₃                      6.

where Me equals the methyl radical.

Instead of attempting to hydrolyze methyl chloride directly to methyl alcohol, the above mechanism provides for the hydrolysis of methyl iodide as shown by equation 2. Because the bond energy between the methyl radical and iodine is much less than is the case for chlorine, the energy of activation is substantially reduced. This lowering of the energy barrier makes for a higher rate of reaction.

The improvement in the reaction rate can be appreciated by some indication of bond energies. Energy values for single bonds are reported by Linus Pauling, *The Nature of the Chemical Bond,* 2$^{nd}$ ed., Cornell University Press, 1948 on page 53. The value for the C—I bond is 45.5 kcal per mole compared with 66.5 kcal per mole for the C—Cl bond. These data indicate that methyl iodide is much less stable than methyl chloride and therefore will react more readily.

Other metal cations can act as promoters in the above reaction mechanism. For example, alkali metals may enhance the conversion of methyl chloride to methyl iodide as indicated by equation 1. Also, zinc if present in the catalyst composition may promote the hydrolysis reaction of equation 2. The means by which a promoter functions is not always understood. The determination of the optimum catalyst composition depends in the final analysis on empirical results.

Although experimental data are missing for the proposed reaction mechanism, certain relationships which are reported give credence to this scheme. For example, it is known that the alkali metal iodides, sodium iodide and potassium iodide, react with methyl chloride to form methyl iodide. Furthermore, it is logical to assume that the reaction of equation 2 is driven to completion because of the strong affinity of cupric oxychloride for hydrogen iodide and hydrogen chloride as shown in equation 3. Oxychlorination is represented by equation 4. It is a fact that this reaction occurs at temperatures substantially below the temperature needed for the Deacon Process, in which free chlorine is released. Moreover, chlorine reacts with perchloroethylene to the exclusion of iodine, the equilibrium being unfavorable for reaction of the latter. Finally, it is well known that cuprous chloride reacts with oxygen to form cupric oxychloride.

Equation 5 is analogous to this reaction.

The physical attributes of the catalyst composition are critical to its use. For example, cupric chloride and potassium chloride form an eutectic mixture which melts at 150° C. This mixture is approximately 65 mole percent copper chloride and 35 mole percent potassium chloride. The low melting characteristic of this mix is believed to be significant in the function of the catalyst. A fresh, active catalyst surface is continually exposed to the reactants. The addition of small concentrations of iodides should have a minimal effect on the fusing properties.

The relative volatilities of the catalyst components are also significant. Excessive volatility will lead to uncontrollable losses resulting in catalyst deactivation. In this regard, the addition of an iodide presents little difficulty. The boiling point of potassium iodide is 1330° C. compared with 1500° C. for potassium chloride.

Instead of incorporating an iodide into the catalyst composition, a bromide may be used. In this case, the reaction mechanism is similar to that shown for an iodide. Bromine, being intermediate between chlorine and iodine in activity, most likely will give results that are a compromise.

The significance of developing a new catalyst composition with higher activity cannot be overstated. All catalytic processes are dependent on an effective catalyst.

Undoubtedly the selection of a suitable catalyst is the most difficult challenge. Thus, the catalyst composition of the present invention is seen as a major breakthrough in the development of a new process for methanol synthesis.

The embodiments of the present invention in which exclusive property or privilege is claimed are defined as follows:

I claim:

1. A catalytic process for the conversion of methyl chloride, perchloroethylene, hydrogen chloride and oxygen to methyl alcohol and hexachloroethane, said process incorporating a catalyst comprising cupric oxyhalide which contains a halogen selected from the group consisting of iodine and bromine.

2. A process according to claim 1 in which the cupric oxyhalide has the formula CuICl·CuO.

3. A process according to claim 1 in which the cupric oxyhalide has the formula CuBrCl·CuO.

* * * * *

UNITED STATES PATENT AND TRADEMARK OFFICE
CERTIFICATE OF CORRECTION

PATENT NO : 5,854,168
DATED : December 29, 1998
INVENTOR(S): Stauffer

It is certified that error appears in the above-identified patent and that said Letters Patent is hereby corrected as shown below: On the title page: Item [54] and Col. 1, line 3, In the Title, please change "Catalyst Composition for Methanol Synthesis" to -- Catalytic Process for Methanol Synthesis--.

In the Abstract, line 1, please delete "composition" and insert --process--.

Column 1, line 28, delete "($CCl_3CCl_{13}$) and insert --($CCl_3CCl_3$)--.

Column 2, line 47, delete "($Mel+H_2O \rightarrow MeOH+HI$)" and insert --($MeI+H_2O \rightarrow MeOH+HI$)--.

Column 2, line 57, delete "MeCI" and insert --MeCl--.

Signed and Sealed this

Seventeenth Day of August, 1999

Attest:

Attesting Officer

Q. TODD DICKINSON

Acting Commissioner of Patents and Trademarks